(12) United States Patent
Mohammadi

(10) Patent No.: US 11,819,402 B2
(45) Date of Patent: Nov. 21, 2023

(54) APEX BILEAFLET MECHANICAL VALVE

(71) Applicant: Hadi Mohammadi, Kelowna (CA)

(72) Inventor: Hadi Mohammadi, Kelowna (CA)

(73) Assignee: Angeleno Medical, LLC, Irvine, CA (US)

( * ) Notice: Subject to any disclaimer, the term of this patent is extended or adjusted under 35 U.S.C. 154(b) by 75 days.

(21) Appl. No.: 17/331,245

(22) Filed: May 26, 2021

(65) Prior Publication Data

US 2021/0369448 A1     Dec. 2, 2021

Related U.S. Application Data

(60) Provisional application No. 63/029,852, filed on May 26, 2020.

(51) Int. Cl.
    *A61F 2/24*         (2006.01)

(52) U.S. Cl.
    CPC .... *A61F 2/2403* (2013.01); *A61F 2220/0091* (2013.01); *A61F 2230/0069* (2013.01); *A61F 2230/0076* (2013.01); *A61F 2230/0095* (2013.01)

(58) Field of Classification Search
    CPC ............ A61F 2/2403; A61F 2220/0091; A61F 2230/0069; A61F 2230/0076; A61F 2230/0095
    See application file for complete search history.

(56) References Cited

U.S. PATENT DOCUMENTS

| | | | | |
|---|---|---|---|---|
| 5,071,431 A * | 12/1991 | Sauter | A61F 2/2409 623/2.4 |
| 5,178,631 A * | 1/1993 | Waits | A61F 2/2403 137/527 |
| 5,824,062 A * | 10/1998 | Patke | A61F 2/2403 623/2.26 |
| 6,051,022 A * | 4/2000 | Cai | A61F 2/2403 623/2.33 |
| 6,113,631 A * | 9/2000 | Jansen | A61F 2/2412 623/2.19 |
| 6,183,511 B1 * | 2/2001 | Patke | A61F 2/2403 623/2.28 |
| 6,296,663 B1 * | 10/2001 | Patke | A61F 2/2403 623/2.28 |
| 6,645,244 B2 * | 11/2003 | Shu | A61F 2/2403 623/2.31 |
| 6,730,122 B1 * | 5/2004 | Pan | A61F 2/2403 623/2.1 |
| 7,371,258 B2 * | 5/2008 | Woo | A61L 27/56 623/2.22 |
| 7,871,435 B2 * | 1/2011 | Carpentier | A61F 2/2418 623/2.14 |
| 8,876,897 B2 * | 11/2014 | Kheradvar | A61F 2/2442 623/2.14 |
| 10,278,814 B2 * | 5/2019 | Scorsin | A61F 2/2415 |

(Continued)

*Primary Examiner* — Suzette J Gherbi
(74) *Attorney, Agent, or Firm* — Riverside Law LLP

(57) ABSTRACT

The present invention provides a bileaflet heart valve that has a central flow hemodynamic configuration similar to the human aortic valve. Further, the present invention provides a bileaflet heart valve that successfully removes the incidence of thrombosis. This design minimizes the mechanical resistance against leaflet movement and allows for a greater washing effect to minimize thrombosis.

23 Claims, 12 Drawing Sheets

(56) References Cited

U.S. PATENT DOCUMENTS

| | | | |
|---|---|---|---|
| 2006/0293745 A1* | 12/2006 | Carpentier | A61F 2/2418 623/2.19 |
| 2009/0164003 A1* | 6/2009 | Kheradvar | A61F 2/2442 623/2.1 |
| 2021/0369448 A1* | 12/2021 | Mohammadi | A61F 2/2403 |

\* cited by examiner (a)

(b)

APEX BILEAFLET MECHANICAL VALVE

CROSS-REFERENCE TO RELATED APPLICATIONS

This application claims priority to U.S. Provisional Patent Application No. 63/029,852, filed May 26, 2020, the contents of which are incorporated by reference herein in its entirety.

BACKGROUND OF THE INVENTION

There are nearly 350,000 valve replacement procedures conducted annually worldwide. The age range of the majority of patients with aortic valve pathology in need of replacement is between 60 and 80 years. Among the two main aortic valve symptoms, replacement for aortic insufficiency, aortic stenosis of ~15% is performed much less frequently than for aortic stenosis of ~85%. As of the related diseases to aortic stenosis, there are several of note, including congestive heart failure, syncope, angina, or a combination of both. If left untreated, the life expectancy of patients reduces significantly. For instance, it would be a 50% reduction over a period of 5 years for angina, over a period of 3 years for syncope, and over a period of 2 years for congestive heart failure. Also, these diseases in a small percentage of patients may cause sudden death.

Generally, there are two major types of artificial heart valves: Mechanical Heart Valves (MHVs), which are completely composed of artificial materials, and Bioprosthetic Heart Valves (BHVs), which consist of treated biomaterials. Mechanical heart valves are used to replace diseased human heart valves in approximately 50% of cases. Bioprosthetic heart valves are used in approximately 45% of the remaining cases. Pulmonary autograft valves and human cryopreserved homograft valves represent the remainder of implanted valves. Autografts and homografts exhibit excellent durability after implantation but are not readily available for all patients.

Pyrolytic carbon (LTI) is known to be the most commonly used material for MHVs since late in the 1960's. BHVs are chemically treated animal valves, such as pig (porcine) and cow (bovine). Their geometry and mechanical properties are similar to those of the human valve which is highly desirable. Nevertheless, BHVs are associated with complications such as calcification and tissue regression and will typically suffer systemic failure after roughly 20 years. MHVs are not known for calcification and tissue regression issues but they are rather highly involved in thrombogenic complications for which those patients must always take anticoagulants in order to minimize their corresponding risks. These issues are mainly due to the improper mechanical design of these valves which lead to non-natural hemodynamics around MHVs. The anticoagulation therapy for those patients may increase the incidence of hemorrhagic diseases and may lead to cardiac complications such as endocarditis, hemolysis, etc.

Bileaflet mechanical valves contain two leaflets, one housing, four hinges, and a sewing ring. The leaflets can rotate around the hinges to open and close the valve. The housing serves as a frame for holding the leaflets. The hinges provide rotation for the leaflets in the housing. The sewing ring is a woven material, such as DACRON, surrounding the housing for surgical attachment to the implantation site. The leaflets, housing, and hinge still need improvements from the hemodynamics point of view.

Bileaflet heart valves form three streams when the two leaflets are opened, which is non-symmetric with respect to a center of the heart valve. Non-hermetic compliance with the aortic sinuses leads to non-symmetric flow profile, thus inducing a large velocity gradient and turbulence. Since the bi-leaflet MHV is centrally asymmetric, the two leaflets are not opened synchronously, leading to great recirculation of blood and increasing the burden on the heart. To overcome such deficiencies, bioprosthetic tri-leaflet heart valves are continuously evolved.

Most conventional bileaflet valves such as On-X and St. Jude Medical (SJM), are based on slight modification of material used and geometry of the housing compared to previous models. For example, on the SJM valve the focus was mostly on a modification of the hinge design. In the On-X valves, silicon had been completely removed from its structure, unlike conventional models. Low profile valves (low length to diameter ratio) are prone to tissue ingrowth (pannus). The profile (length to diameter ratio) of the On-X valve is designed to be similar to that of the native aortic valve, therefore providing unique protection from tissue damages on both the inflow and outflow sides. An inlet flare, full annulus support, and leaflet guards are all components in the design. The opening angle is considered to be 90° (>80° in SJM), which is thought to improve the hemodynamics of the valve significantly. The design of the pivot hinge is also improved, which may in turn lead to more stability of the hinges and less thromboembolic complications. Pivots are high potential sites of clot formation, due to the possibility of flow stagnation (stasis). In the On-X design, the location and geometry of the hinges were designed so they are being constantly washed out in every cardiac cycle more efficiently compared to conventional valves. This is done to eliminate possible flow stagnant regions around the hinges. The backflow channels are sensibly designed in order to avoid hemolysis by allowing blood flow to penetrate the pivot areas. The improved hemodynamics provided in the On-X valve is thought to decrease the anticoagulation therapy in low-risk patients. This valve has been implanted in many patients to date in both the aortic and mitral positions and together with the St. Jude Medical valve are the most widely implanted prosthetic valve alternatives considered by cardiac surgeons globally.

There is a need in the art for an improved valve prosthetic that has a central flow hemodynamic configuration similar to the human aortic valve and a bileaflet heart valve that successfully removes the incidence of thrombosis. The present invention meets this need.

SUMMARY OF THE INVENTION

In one aspect, the present invention relates to a mechanical bileaflet heart valve device, comprising: a ring-like housing having a saddle-shaped curvature and an elliptical top-down profile that defines an elliptical central orifice for blood flow therethrough; and two substantially hollow cylindrical-wedge-shaped curved leaflets hingedly attached to an interior of the housing, wherein each leaflet is rotatable between a closed position that completely seals the central orifice and an open position that completely opens the central orifice.

In one embodiment, the central orifice comprises a major axis diameter and a minor axis diameter. In one embodiment, the major axis diameter is between about 15 mm and 40 mm. In one embodiment, the minor axis diameter is between about 10 mm and 35 mm. In one embodiment, the saddle-shape curves downwards towards the major axis diameter and curves upwards towards the minor axis diameter. In one embodiment, the leaflets are hingedly attached to the housing at opposing downward curving sections adjacent to the major axis diameter. In one embodiment, the housing comprises an opposing pair of inward facing semi-spherical nodal bumps positioned on opposing upward curving sections in alignment with the minor axis diameter. In one embodiment, each leaflet rests against each nodal bump in the open position.

In one embodiment, the cylindrical-wedge-shape of the leaflets comprises two curved lateral halves that curve symmetrically from a central crest and terminate in two opposing tips, each tip comprising an outward facing hinge projection. In one embodiment, the hinge projections of the leaflets engage inward facing hinge sockets in the housing to form the hinged attachment between the leaflets and the housing. In one embodiment, the hinged attachment is configured to be exposed to and continually washed by a flow of blood such that thrombosis incidence is reduced. In one embodiment, the hinge projections and the hinge sockets each comprise a substantially hourglass shape. In one embodiment, the hinge projection is slightly smaller than the hinge socket, such that a degree of sliding motion is achievable between the leaflets and the housing.

In one embodiment, the leaflets each comprise a superior curved leading edge and an inferior curved trailing edge. In one embodiment, the leading edges of the leaflets meet each other in a center of the central orifice and the trailing edges of the leaflets meet the housing in the closed position. In one embodiment, the leading edge is configured to travel for a travel angle between the closed and open positions, wherein the travel angle is between about 30° and 50°. In one embodiment, the trailing edge is formed at an angle above a horizontal plane, wherein the angle is between about 0° and 25°. In one embodiment, the trailing edge is formed at an angle above a horizontal plane, wherein the angle is half of the travel angle.

In one embodiment, the housing comprises a sewing ring positioned on an outward facing surface. In one embodiment, the sewing ring is made of a woven or knitted fabric.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
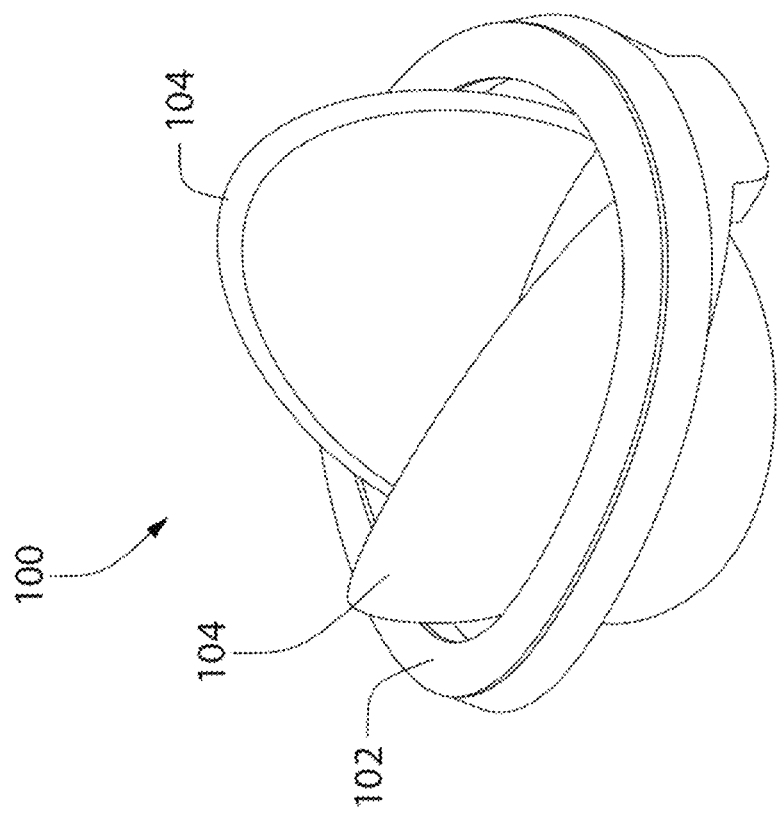
FIG. 1 depicts isometric views of an exemplary mechanical bileaflet apex valve. The apex valve is shown in a closed position (left) and an open position (right).
Figure 1:
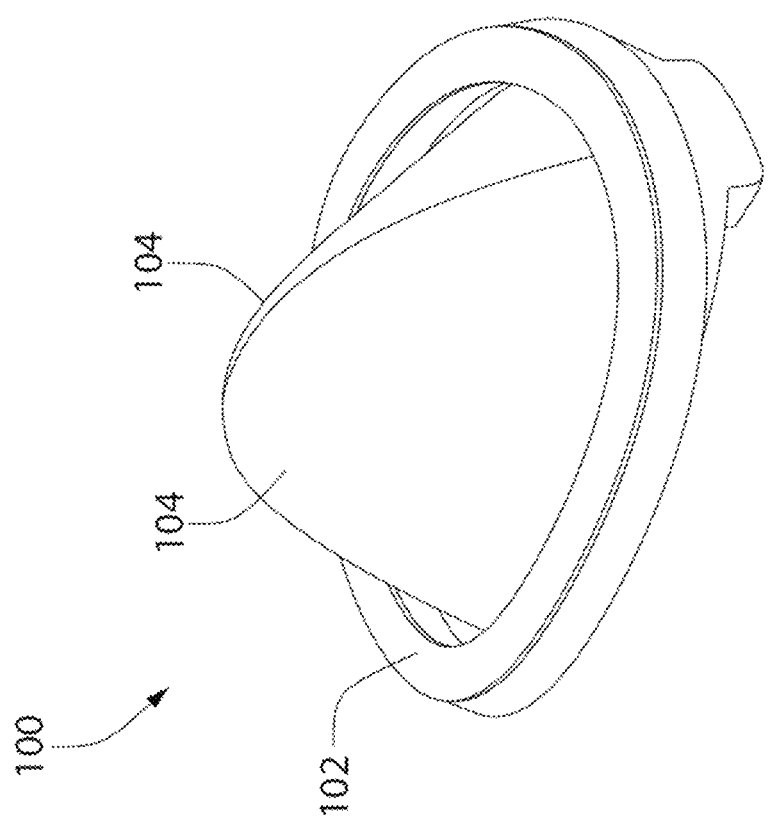

The present invention provides a bileaflet heart valve that has a central flow hemodynamic configuration similar to the human aortic valve. The pressure induced by blood circulation inside the semi-circular aortic sinuses downstream the heart valve assists in opening and closing the leaflets. Further, the present invention provides a bileaflet heart valve that successfully removes the incidence of thrombosis. The design of the hinge mechanism is improved. A pivot joint between the valve leaflets and the housing is formed by a curved projection and "butterfly" hinge projections on the leaflet, which allows for rotation and sliding of the leaflet with respect to the housing. In this model, the housing has "butterfly" hinge sockets shaped correspondingly to the hinge projections of the leaflets. This design minimizes the mechanical resistance against leaflet movement and allows for a greater washing effect to minimize thrombosis.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Mechanical Bileaflet Apex Valve

The present invention provides mechanical bileaflet heart valves that provide multiple design features and benefits of bioprosthetic valves, including but not limited to: saddle-shaped stents, central flow, a large orifice area, leaflets that are completely in contact with a stent when the valve is fully open, minimal closing phase, minimal opening phase, and minimal regurgitation flow. Typical mechanical heart valves present 3 orifices that divide the bloodstream and decrease valve efficiency. In contrast, the mechanical heart valves of the present invention have only a single orifice with minimum closing angle configured to minimize closing phase and regurgitation flow and maximum opening angles configured to minimize disturbance to blood flow and improve hemodynamics. A shorter opening phase further reduces thrombogenicity.

Referring now to FIG. 1, an exemplary mechanical bileaflet apex valve 100 is depicted. Apex valve 100 comprises a ring-like housing 102 encircling two leaflets 104. Apex valve 100 represents a substantial improvement over existing heart valves in at least three aspects: housing 102 comprising an optimal saddle shape configured to provide ideal maximum opening and closing angles for leaflets 104 in order to minimize opening and closing phases, thereby reducing regurgitation flow; leaflets 104 comprising an optimal curved shape configured to provide maximum orifice area and minimum flow disturbances when fully open; and hinged connections between housing 102 and leaflets 104 configured to receive more shear and wash than existing heart valves.

Figure 2:
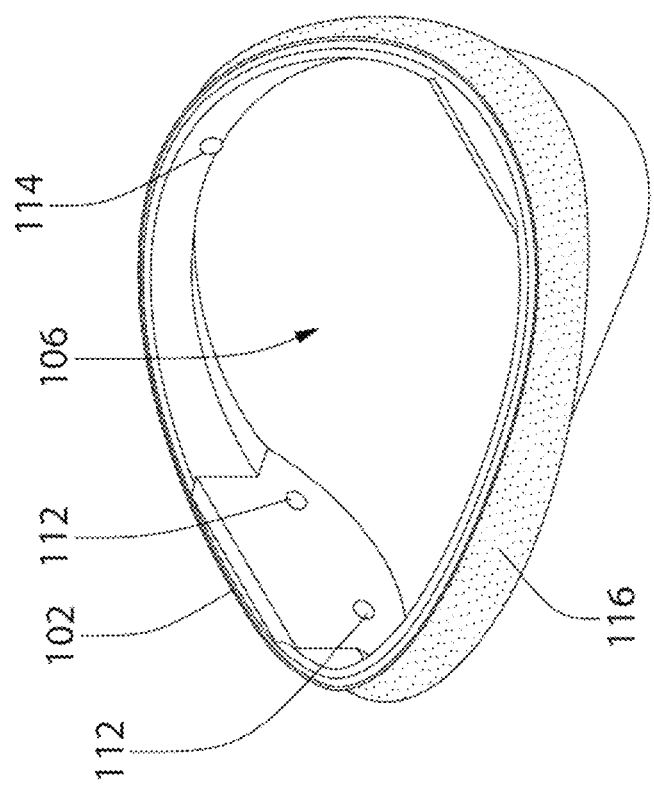
FIG. 2 depicts isometric views of an exemplary apex valve housing. The left image depicts a line drawing; the right image depicts a rendering with a sewing ring attached.
Figure 2:
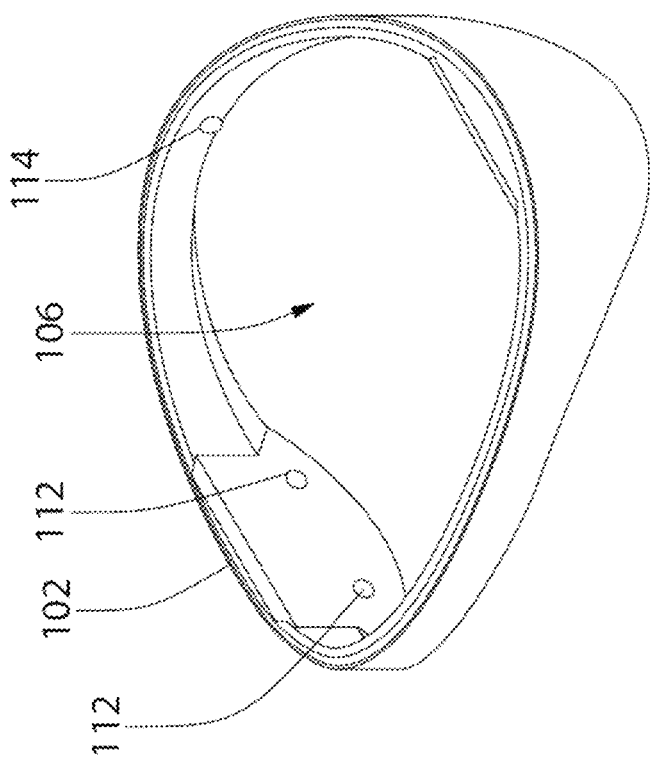
Figure 3:
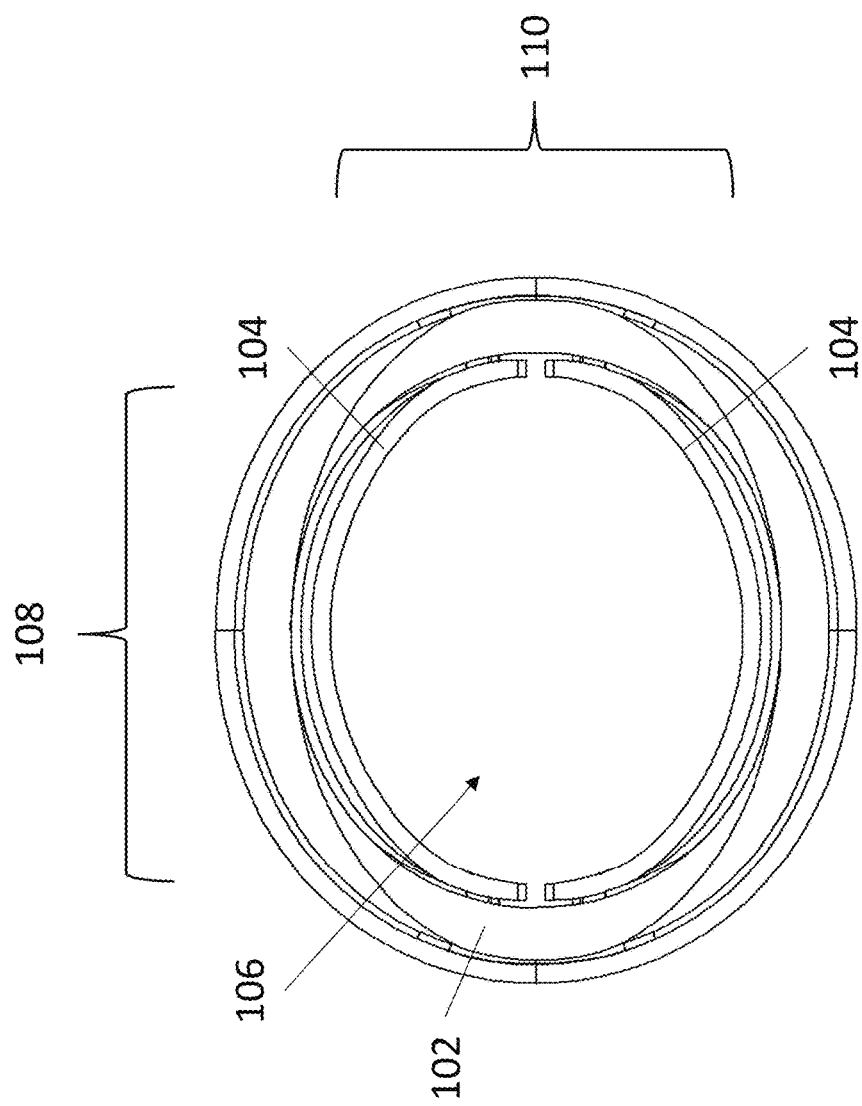
FIG. 3 depicts a top-down view of an exemplary apex valve in an open position.

Referring now to FIG. 2 and FIG. 3, an exemplary housing 102 is described in detail. Housing 102 is a ring-like structure having a saddle-shaped curvature and an elliptical top-down profile with an elliptical central orifice 106, wherein central orifice 106 has a major axis diameter 108 and a minor axis diameter 110. Housing 102 can comprise any desired dimensions, including but not limited to a major axis diameter 108 between about 15 mm and 40 mm, such as about 27 mm, and a minor axis diameter 110 between about 10 mm and 35 mm, such as about 23 mm. In some embodiments, major axis diameter 108 and minor axis diameter 110 are proportional to each other such that housing 102 comprises an ovality of 10%, wherein ovality is calculated by double the difference between major axis diameter 108 and minor axis diameter 110 divided by the sum of major axis diameter 108 and minor axis diameter 110. Housing 102 comprises a low profile to minimize transvalvular pressure. In some embodiments, the saddle-like shape of housing 102 curves downwards towards major axis diameter 108 and curves upwards towards minor axis 110. Housing 102 comprises two pairs of opposing hinge sockets 112 positioned adjacent to the downward curving major axis diameter 108, wherein each pair of opposing hinge sockets 112 are configured to receive a pair of opposing hinge projections 118 of a leaflet 104, as will be described elsewhere herein. In some embodiments, housing 102 comprises a set of opposing nodal bumps 114 positioned on an upward curving portion, such as a position aligned with minor axis diameter 110. Nodal bumps 114 are semi-spherical structures that form a stop against which leaflets 104 rest against when in an open position. Accordingly, nodal bumps 114 create a small space between each leaflet 104 and housing 102 to prevent blood from being trapped behind each leaflet 104. Housing 104 further comprises a sewing ring 116 positioned along an outer surface. Sewing ring 116 can comprise a woven or knitted fabric, such as Dacron.

Figure 4:
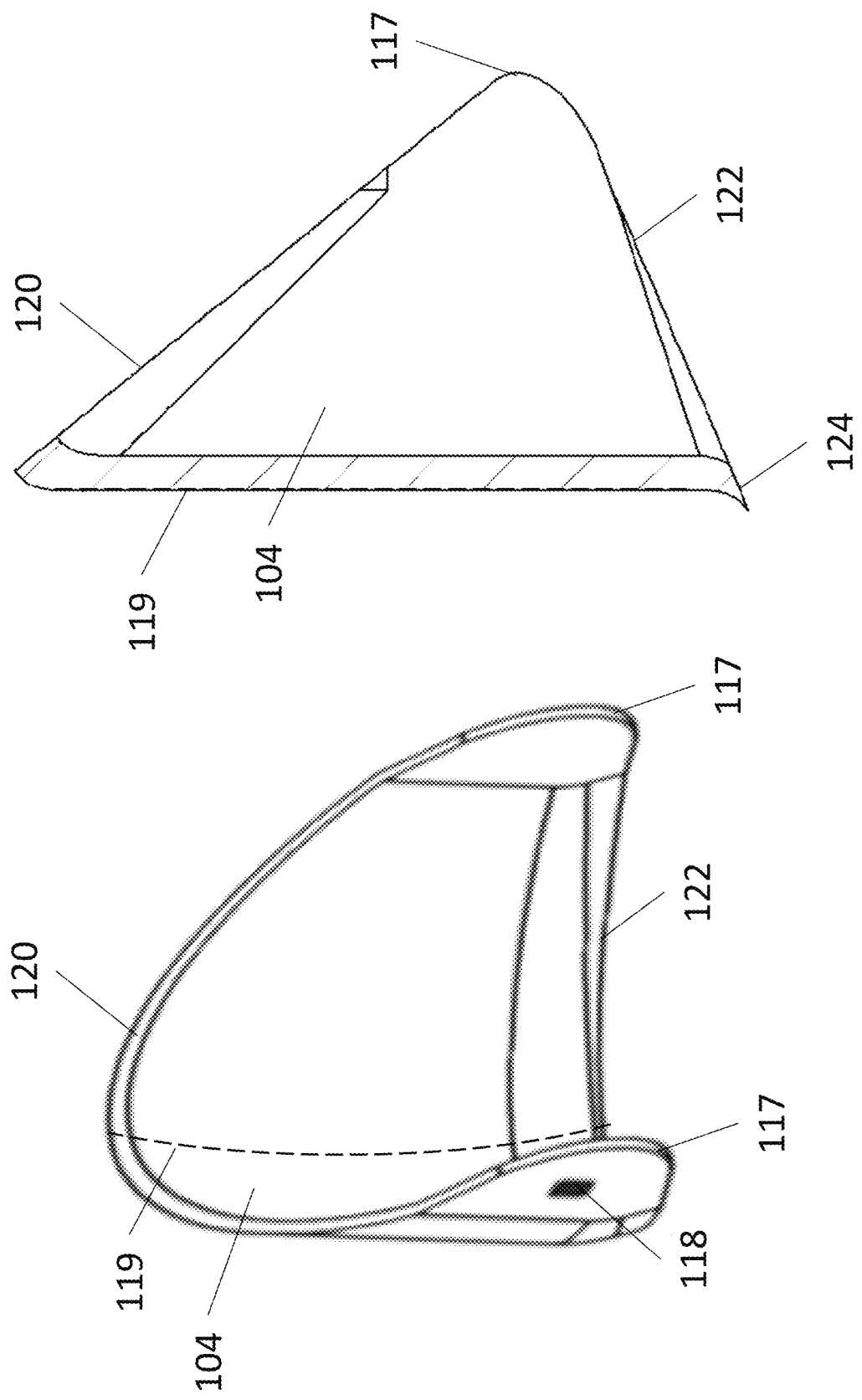
FIG. 4 depicts an isometric view (left) and a side partial sectional view (right) of an exemplary apex valve leaflet.
Figure 5:
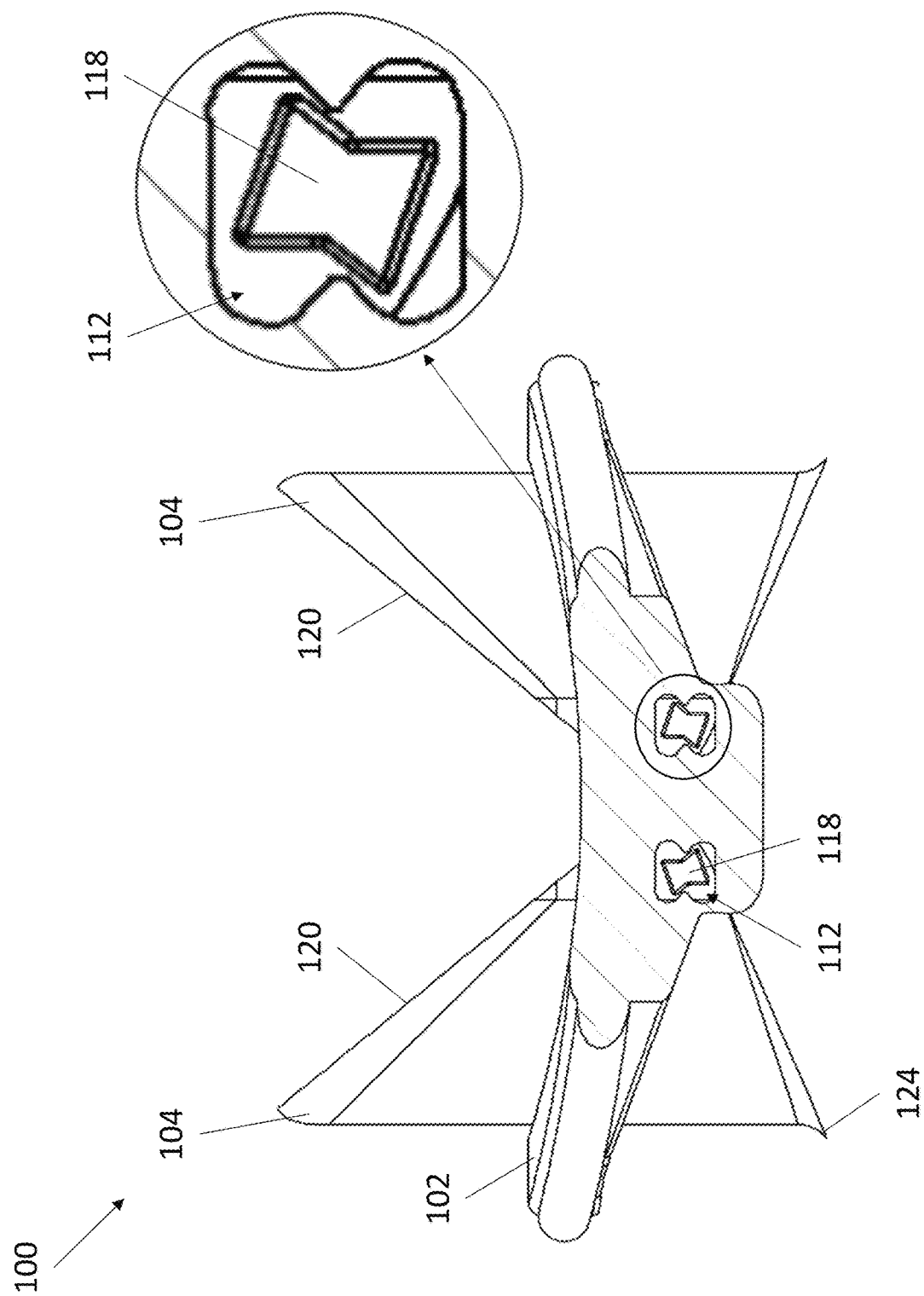
FIG. 5 depicts a side partial sectional view of an exemplary apex valve hinge in an open position. A magnified view of the hinge is shown in the inset.
Figure 6:
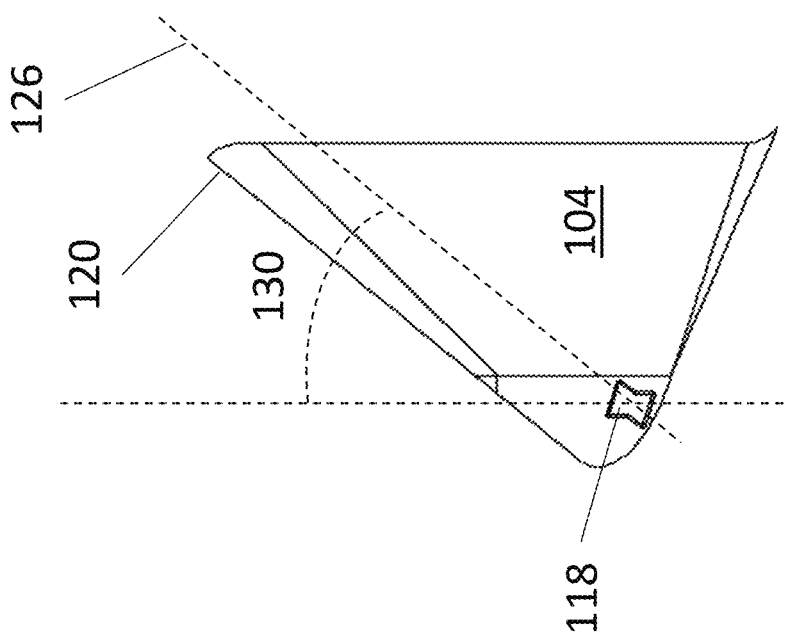
FIG. 6 depicts a side view of an exemplary apex valve leaflet. The left image depicts two leaflets in a closed position. The right image depicts a leaflet in an open position.
Figure 6:
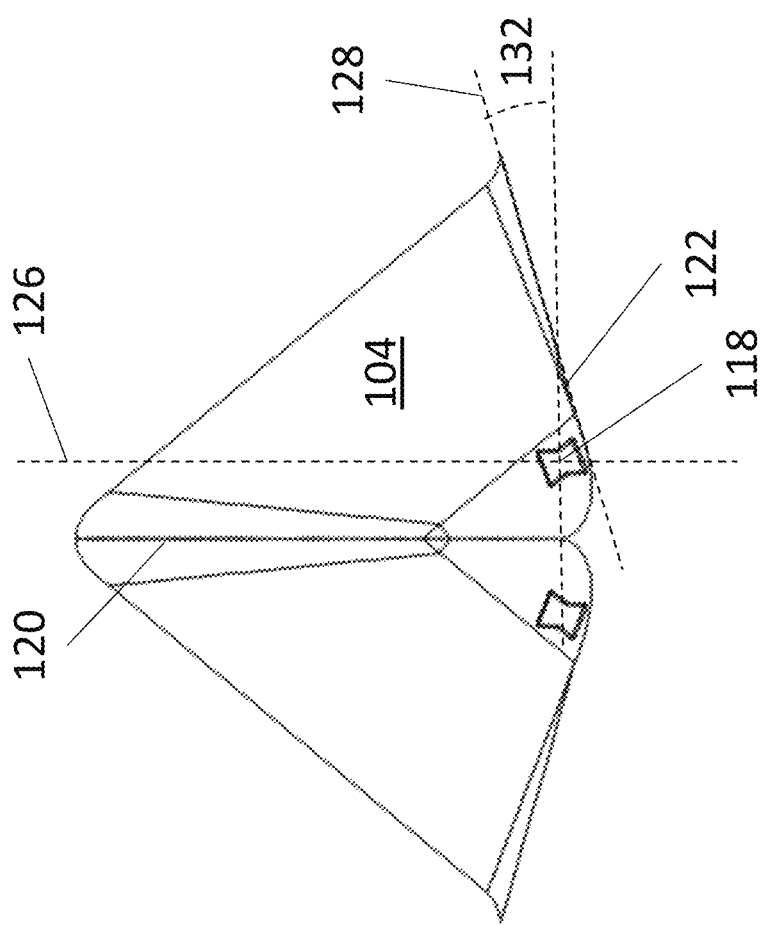

Referring now to FIG. 4 through FIG. 6, leaflets 104 are now described in detail. Leaflets 104 have a substantially hollow cylindrical-wedge shape formed by two curved lateral halves that curve symmetrically from a central crest 119 and terminate in two opposing tips 117, wherein each tip 117 comprises an outward facing hinge projection 118. Leaflets 104 comprise a superior curved edge forming a leading edge 120 and an inferior curved edge forming a trailing edge 122. Leading edge 120 comprises an overextension in a radial direction when in an open position, the extension being between about 0.1 mm and 1 mm, or about 0.58 mm. Leading edge 120 is perpendicular with a closed position plane, allowing for a soft closure of leaflets 104. In some embodiments, trailing edge 122 further comprises an edge flare 124, wherein edge flare 124 is configured to extend radially to decrease leakage volume between leaflets 104 and housing 102 in a closed position. Edge flare 124 can also improve valve mobility during opening and closing phases. Edge flare 124 can extend for any desired distance, such as between about 0.5 mm and 1.5 mm. Leaflets 104 comprise a curved body that conforms substantially to central orifice 106 of housing 102, as is evidenced by FIG. 3, such that leaflet 104 has a width that spans major axis diameter 108 and a depth about half of minor axis diameter 110. In a closed position, leading edge 120 of each leaflet 104 meet in the center of central orifice 106 to form a seal aligned along major axis diameter 108, and trailing edge 122 or edge flare 124 meet an inner surface of housing 102 to form a seal along an inner circumference of housing 102, thereby sealing central orifice 106. In an open position, leaflets 104 rotate away from each other such that central crest 119 of each leaflet 104 are aligned substantially vertically relative to housing 102 and rest against nodal bump 114. Leaflets 104 can have any desired thickness, such as a thickness between about 0.5 mm and 2 mm, or about 1 mm. In some embodiments, leaflets 104 comprise a uniform thickness throughout.

Hinge projections 118 of leaflets 104 are configured to seat within a hinge socket 112. The engagement between a hinge projection 118 and a hinge socket 112 is shown in FIG. 5. Hinge socket 112 has a first shape similar to an hourglass, butterfly, or bowtie, and hinge projection 118 has a second hourglass, butterfly, or bowtie shape that is smaller than the first shape, permitting hinge projection 118 to rock back and forth within hinge socket 112 and allowing leaflets 104 to rotate between closed and open positions. Hinge projection 118 can have any desired dimensions, such as a length and width of about 1.5 mm with a central tapering to a width of about 1 mm. Importantly, hinge socket 112 and hinge projection 118 are exposed, such that blood flow constantly washes the hinged engagement to discourage thrombosis formation. In some embodiments, the first shape and the second shape may be slightly mismatched, such that a leaflet 104 may slide about within hinge sockets 112 in addition to rotational movement to further encourage washout of the hinged engagement. In certain embodiments, the orientation of hinge socket 112 and hinge projection 118 may be reversed, such that hinge projections 118 are positioned on housing 102 and hinge sockets 112 are positioned on leaflets 104.

Leaflets 104 can further be characterized by leading edge travel angle 130 and trailing edge rise angle 132, as shown in FIG. 6. In a closed position, leading edges 120 of both leaflets 104 meet flush to form a tight seal. Accordingly, leading edges 120 are aligned vertically along leading edge axis 126. Trailing edge 122 is in alignment with a trailing edge axis 128 that is angled relative to a horizontal axis by a trailing edge rise angle 132. Trailing edge rise angle 132 can be any angle, such as an angle between about 0° and 25°, or about 10°, with greater angles leading to shorter leaflet lengths. In an open position, leaflet 104 rotates along hinge projection 118 such that central crest 119 of leaflet 104 is substantially vertical and rests against a nodal bump 114. In the open position, leading edge 120 has traveled by a leading edge travel angle 130. Leading edge travel angle 130 can be any angle, such as an angle between about 30° and 50°, or about 40°. In various embodiments, the dimensions of leaflet 104 can be tuned to fit a particular patient or subject. In some embodiments, trailing edge rise angle 132 is set equal to half of travel angle 130.

The optimized shape of leaflets 104 allows for the closing and opening angles of the leaflets 104 to be reduced in comparison to traditionally straight leaflets. The curved leading edge 120 of leaflets 104 is configured to capture energy from blood flow to assist with the closing and opening movements. The curved nature of leaflets 104 along their length also assist in capturing energy from the blood flow. The minimization of surface area was a key focus throughout this design and can be seen in the shape of housing 102. The cross-sectional area was reduced as much as possible while still allowing for structural rigidity and ideal hinge placement. These reductions allow for leaflets 104 to be smaller as well. The contact point between leaflets 104 when closed is linear instead of planer to reduce the chances of red blood cell lysis. When closed, leaflets 104 also contact housing 102 at the bottom along a linear profile. The contact between leaflets 104 and housing 102 when open is at a single nodal bump 114 to further reduce the probability of damage. Leaflets 104 do not make contact with each other in the open position. By having housing 102 act as a stopping point for leaflets 104, the forces exerted on leading edges 120 of leaflets 104 and the hinges is reduced significantly. In the open position, leaflets 104 move almost entirely out of the path of blood flow. This allows for a significantly improved lumen and reduces disturbance experienced by the blood flow as the majority of flow passes through the center of apex valve 100. Since flow through apex valve 100 is through a single orifice the chances for unwanted oscillatory flow are reduced as there is no longer a difference in flow velocity. Hemodynamics can further be improved by matching the natural ovality of heart valves. Widening the housing and lengthening the leaflets could closely match the shape of a native valve of a patient or subject and further improve flow. Accordingly, apex valve 100 of the present invention provides the following advantages over existing heart valves: improved wash in the hinge area; improved shear stresses around and downstream of the valve; minimum transvalvular pressure; reduced regurgitation; no high shear stress zones created; and no regions of flow stagnation or separation.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, utilize the present invention and practice the claimed methods. The following working examples therefore, specifically point out exemplary embodiments of the present invention, and are not to be construed as limiting in any way the remainder of the disclosure.

Example 1

History of bileaflet mechanical heart valves (MHVs) (Mohammadi H, 2017, Cardiovascular Systems, 5(2)): The design of bileaflet mechanical heart valves goes back to the 60's. In 1964, the Kalke-Lillehei bileaflet valve was introduced. This valve was the first ever design of bileaflet mechanical valves with a pivot mechanism. In this design, the pivot sites for the two solid leaflets were located at the equator of the housing or annulus. This design was associated with major hemodynamic complications and accordingly its fabrication was stopped mainly because of that and the lack of an appropriate biomaterial for this model. In 1977 the design of St. Jude Medical valve was introduced. This design was conceptually similar to the design of the Kalke-Lillehei valve, however, the focus was more on the improvement of the pivot hinge. In this model, both the leaflets and the housing were made of Pyrolyte, which made the St. Jude valve the first ever valve made entirely of carbon. This model was a success and soon became a major alternative for the replacement of the diseased valves. This valve has been implanted millions of times in patients in both the aortic and the mitral positions. In 1986, Carbomedic bileaflet valve was introduced which was conceptually similar to St. Jude Medical valve. In this valve, both the leaflets and the housing were made of Pyrolyte and the main feature was the housing that could rotate with respect to the sewing ring. This valve was marketed as the Carbomedics bileaflet valve and was implanted in more than 350,000 patients in the aortic position and in 250,000 patients in the mitral position. The ATS valve was introduced in 1994. The ATS bileaflet valve, similar to the St. Jude medical valve, was a new design of bileaflet heart valve that was made of Pyrolyte in 1994. This model was branded as the ATS Open Pivot valve prosthesis. The ATS bileaflet valve is thought to provide a better hemodynamics and less noise compared to other bileaflet valves. This valve has been implanted in nearly 1200 patients in both the aortic and the mitral positions from 1994 to 2000. In 1996, the design of On-x valve was introduced. This model was an overall improvement 87 on St. Jude medical bileaflet valves. This valve has been implanted in so many patients so far in both the aortic and the mitral positions and together with St. Jude Medical valve are the most widespread prosthetic valves alternative considered by cardiac surgeons globally. A few years later Sorin valve was introduced to the market. The idea behind the Sorin bileaflet valves was to design and fabricate an advanced version of the original bileaflet model, which would overcome some of its inherent deficiencies and surpass its performance. Maximal hemodynamic performance was achieved with the design of the curved leaflets and the aerofoil inner housing profile. Structural stability and excellent mechanics resulted from the choice of a titanium alloy for the housing when combined with the decreased thrombogenicity of the pyrolitic carbon coating. The hinge design was based on the principle of rolling without sliding.

A brief history on the development of MHVs: The introduction of ball and cage valves was a major advancement in the treatment of patients with valvular heart disease (Mohammadi H, Mequanint K, 2011, Med Eng Phys., 33(2): 131-147). While the importance of ball and cage valves in the history of medicine remains undisputable, it is common knowledge today that these valves are associated with multiple complications such as high pressure drops and poor hemodynamics (Mohammadi H, 2017, Cardiovascular Systems, 5(2)). In order to improve these valves, from an engineering standpoint, the ball in these valves could be replaced by a disc. A lighter and swifter disc could improve dynamic response, the closing and opening phase times, and reduce the regurgitation flow of the valve. However, providing improved hemodynamics by a disc and cage valve would be far from guaranteed (Mohammadi H, 2017, Cardiovascular Systems, 5(2)). An engineering solution for addressing this issue was if the motion of the disc in a disc and cage valve could be imposed by a strut. In other words, the high pressure-drop across the disc, the disrupted blood flow due to the geometry of the disc, e.g., turbulent flow downstream of the valve, could be addressed easily by replacing 110 the floating disc with a tilting disc (Mohammadi H, 2017, Cardiovascular Systems, 5(2)). The next obvious idea was how to incorporate a central flow to tilting disk valves, which by their design, occluded the central region of the valve. The resolution seemed to be trivial. It was possible by breaking the disc from a disc and cage valve into two symmetrical semi-circular components or leaflets, each pivoted to the housing by hinges. The new idea could provide improved hemodynamics compared to earlier valve designs since the area where the velocity of blood is expected to be maximum, is now wide open. In this concept, the leaflets opening and closing angles are constrained to hinges shaped like a butterfly's wings. Even though MHVs are undisputedly extremely successful, the hemodynamic complications associated with bileaflet MHVs causing thrombogenicity and RBC lysis remain as major issues (Mohammadi H, et al 2015, Cardiovasc Syst., 3(1):1-6; Jahandardoost M, et al, 2016, Proc Inst Mech Eng Part H J Eng Med., 1-16; Jahandardoost M, et al, 2016, Proc Inst Mech Eng Part H J Eng Med., 230(2):85-96). In an attempt to improve the design of bileaflet MHVs, an oval design was suggested for the housing of the SJM valve (Mohammadi H, et al 2015, Cardiovasc Syst., 3(1):1-6; Mohammadi H, et al., 2017, Cardiovascular Systems, 5(2)) and then its hemodynamics were computationally studied and compared with that of the SJM valve in both the closing (Mohammadi H, et al 2015, Cardiovasc Syst., 3(1):1-6; Mohammadi H, et al., 2017, Cardiovascular Systems, 5(2)) and the opening phases (Jahandardoost M, et al, 2015, J Eng Med., 229(3):232-244; Jahandardoost M, et al, 2016, Proc Inst Mech Eng Part H J Eng Med., 1-16; Jahandardoost M, et al, 2016, Proc Inst Mech Eng Part H J Eng Med., 230(2):85-96) by setting the heart rate (HR) on 72 bpm. Additionally, a comprehensive computational study was performed on the proposed and conventional models in order to assess their hemodynamics in a variety of HRs ranging from 70 bpm to 150 bpm (Jahandardoost M, et al, 2018, J of Mechanics in Medicine and Biology, 18(2):1850014). Consequently, the idea of an oval housing for bileaflet MHVs was a success and improved hemodynamic performance for the proposed model was achieved. This achievement was characterized by lower shear stress and wall shear stress within the valve and beyond, and a lower transvalvular pressure (Jahandardoost M, et al, 2015, J Eng Med., 229(3):232-244; Jahandardoost M, et al, 2016, Proc Inst Mech Eng Part H J Eng Med., 1-16; Jahandardoost M, et al, 2016, Proc Inst Mech Eng Part H J Eng Med., 230(2):85-96). In this current study, a new concept is introduced for the design of MHVs aimed at the hinges, housing, and leaflets: the apex bileaflet MHV.

Methods:

Design Procedure:

The primary objective for the apex valve is to design a bileaflet MHV that offers hemodynamics similar to that of the native valve. This successful hemodynamic performance is validated if the proposed valve provides: (1) Central flow to the blood stream, (2) Sufficient shear stress/wash in the hinges area, (3) Maximum effective orifice area through a single pathway, (4) Short (comparable to tissue valves) opening and closing phases, (5) Minimum contact surfaces between the blood and the valve, (6) Minimum transvalvular pressure, (7) No turbulent flow, (8) No high shear stress regions within the valve and beyond (except for the hinges), (9) No stagnation or separation regions, and (10) Minimum closing volume.

Design of Housing:

As shown in FIG. 2 and FIG. 3, an optimal saddle-shaped housing is proposed in order to provide the ideal maximum opening and closing angles which will minimize valve opening and closing periods, and thus, lower the closing volume. Ovality is also introduced to the housing to mimic the native annulus shape. The design of the housing will provide a minimum closing angle of the valve which is set to 60°, such to significantly improve the closing phase and reduce the closing volume. The maximum opening angle is set to 89°, which leads to less disturbance to the blood flow and an improved hemodynamic performance. Also, the suggested opening and closing angles will lead to a shorter opening phase causing less thrombogenicity.

Design of the Leaflets:

As shown in FIG. 1, the optimally curved leaflets are designed in order to maximize the orifice area and minimize the flow disturbance in the opening and forward flow phases when the valve is fully open.

Hinges:

The design of the hinges is significantly improved in order for the hinge areas to be more exposed to the blood stream and experience sufficient shear stress (known as wash). A pivot joint between the leaflets and the housing is formed by a curved projection and a semi-circular smooth socket on the leaflet (FIG. 12), which allows for rotation and sliding of the leaflet with respect to the housing. In this design, the housing protrudes into the leaflets which is expected to minimize the mechanical resistance against leaflet movement and allows for greater washing effect, minimizing its thrombogenicity.

Figure 9:
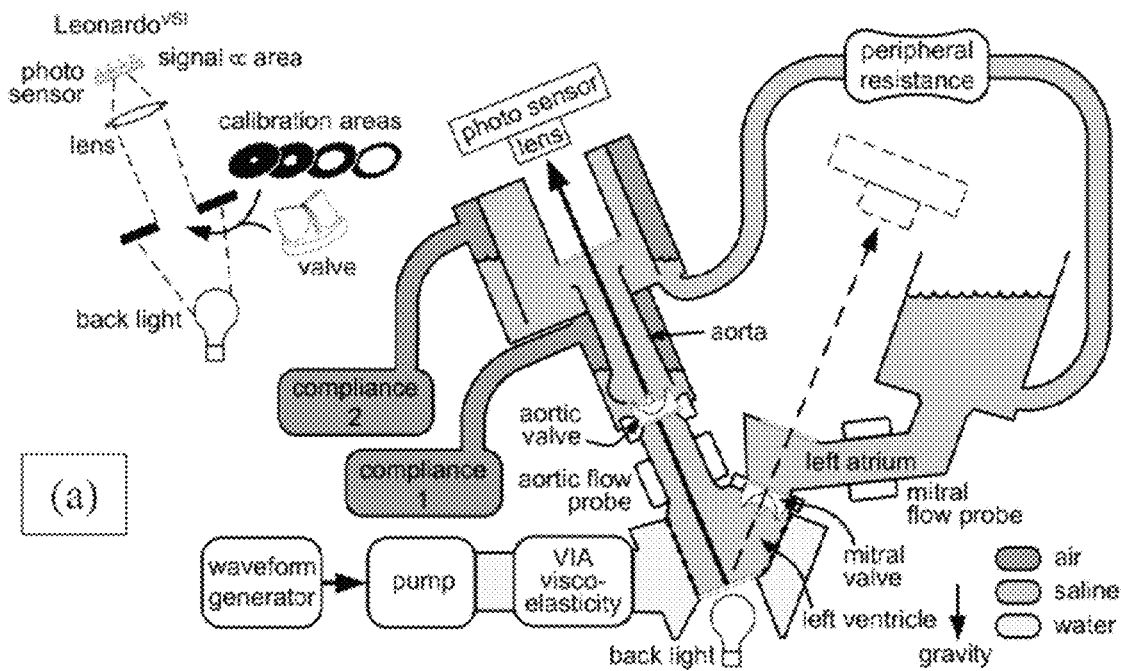
FIG. 9 depicts (a) the testing platform used for an in vitro study on the apex valve. At upper left, the elementary in situ measurement and calibration features of the Leonardo VSI apparatus is shown. This apparatus as shown includes the photosensor, back light, and lens and provides a high spatiotemporal resolution of the projected dynamic valve area (PDVA) in a full cardiac cycle (Scotten L S, Siegel R, 2011, The Journal of Heart Valve Disease, 20:664-672). (b) The apex valve mounted in the aortic position on Leonardo apparatus for in vitro testing.
Figure 9:
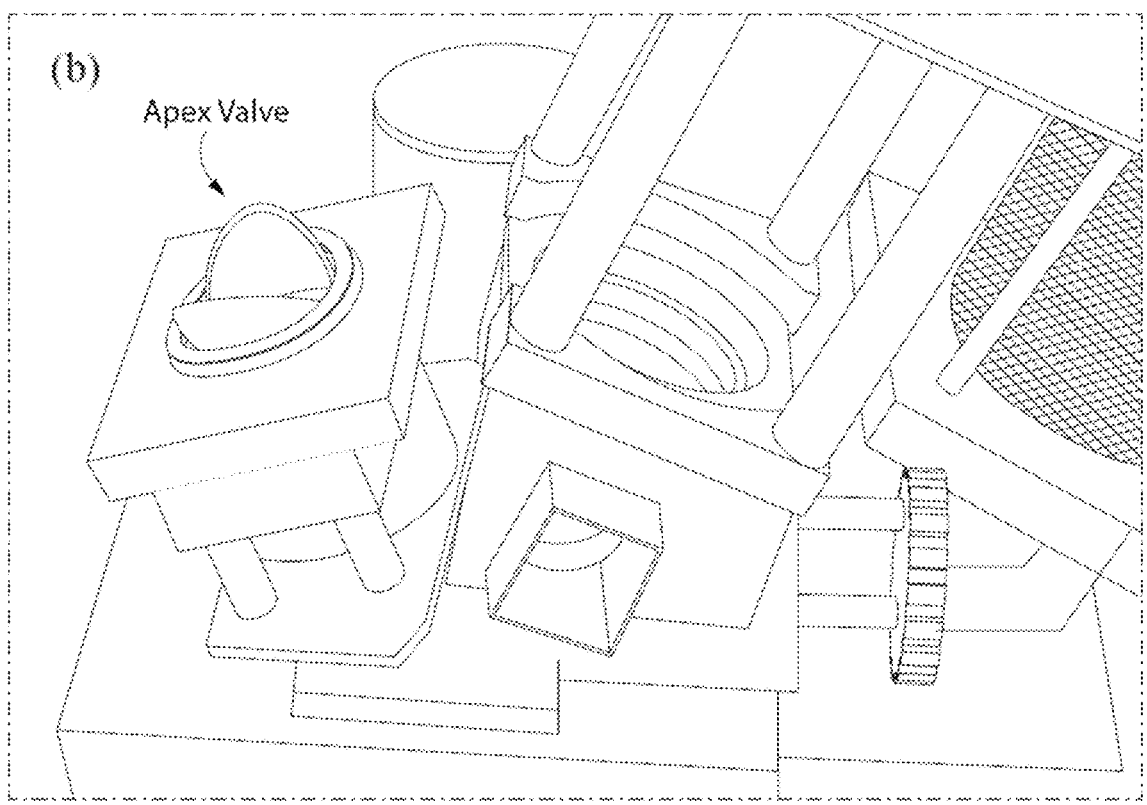

The Assembled Design:

The curved edge provided on the leaflet tips is intended to facilitate the closing and opening movements of the valve as shown in FIG. 9. The minimization of contact surfaces between the valve and blood was a key focus throughout this design. The contact between the leaflets and the housing when the valve is fully open is designed to be nodal. Also, a small semi spherical appendage is provided on the housing so that it causes a small space between the leaflets and housing when the valve is fully open. This design avoids blood flow from trapping behind the leaflets so that the risk of RBC lysis behind the leaflets is minimized.

The leaflet maximum and minimum motions are limited by the housing by which the housing and the leaflets are designed to follow a simple 4-bar-link mechanism. A single orifice for the blood stream was incorporated to reduce the chances of unwanted oscillatory flow since the core of the blood flow moves undisturbed through the valve.

Numerical Modeling:

A quick and sufficiently precise original numerical model was established to estimate the overall performance of the new design. The improved hemodynamics in the suggested design is characterized by the regurgitation volume and velocities of blood and the leaflet tip in the closing phase. The proposed numerical model is based on the finite strips method to solve the equations of motion using 4th order Runge-Kutta method and is run on an Intel® Core™ i7-4500u CPU @1.80 GHz &1.80 GHz processors with 16.0 Gb of RAM.

Figure 7:
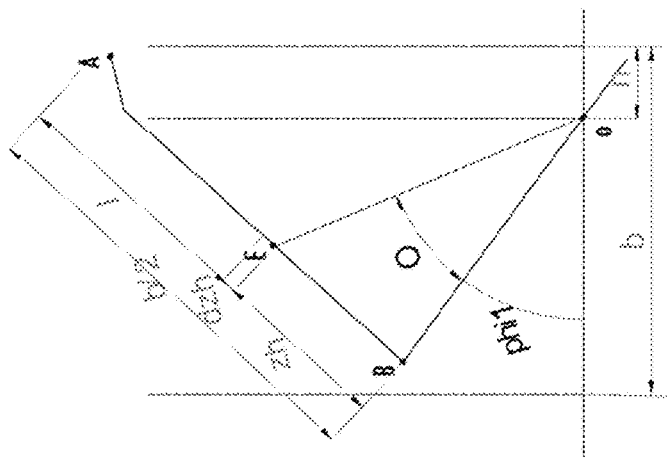
FIG. 7 depicts a diagram showing a control volume defined around an apex valve. The line segment defined by vertices oBA is the leaflet, the vertex o is the hinge, the vertex A is the leaflet tip, the length b is the minor diameter of the elliptic housing, the length h is the distance of o from the valve center, the distance between vertex A and vertex D is the inlet, the distance between vertex B and vertex C is the outlet, y is the distance between the inlet and an arbitrary section, e.g., EF, phi is the angular stroke of leaflets, $zh+1=m$ is the height of the valve, 0 is the angle between line segment OB and OE.
Figure 7:
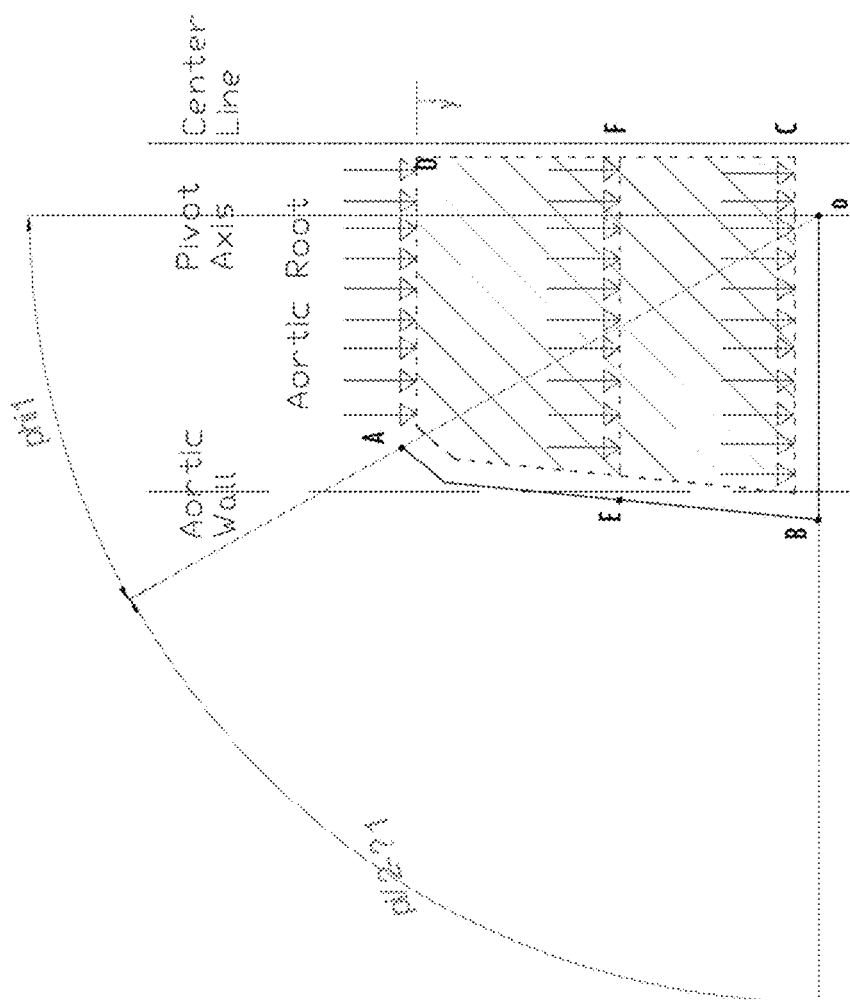

In order to simulate the regurgitation flow from the aortic root to the left ventricle, a half symmetrical model of the valve was applied. By the initiation of the closing phase, the ventricular (Pv) and aortic pressures (Pao) are equal and assumed to be constant (Mohammadi H, et al, 2017, Cardiovascular Systems, 5(2)). A control volume was defined around the valve as demonstrated in FIG. 7 in which OBA shows the leaflet pivoted at O (OBA is essentially a 3D curve). EF is the section of interest, AD and BC referring to the inlet and outlet and blood velocities at those sections are VEF, VAD, and VBC, respectively. AD and EF are separated by a distance of "y". BC (b) is half of the minor diameter of the valve while the major diameter is denoted as "a", as shown in FIG. 7. It is assumed that the gradient of velocities and pressure from top (inlet) to bottom (outlet) remains linear. The velocity of the arbitrary section, EF, is calculated with respect of the blood velocities at the inlet (VAD) and the outlet (VBC) using the continuity equation applied to the control volume with moving boundaries as such (Mohammadi H, et al, 2017, Cardiovascular Systems, 5(2)):

$$a\ AD(V_{AD} - V_{tAD}) = a\ EF(V_{EF} - V_{tEF}) + \frac{dV_i}{dt} \quad (1)$$

$$V_{tAD} = OA\ \omega\ \cos\theta \quad (2)$$

$$V_{tEF} = OE\ \omega\ \cos\theta \quad (3)$$

$$V_i = \frac{(AD+EF)}{2} a\ ED\ \sin\theta \quad (4)$$

Here, $V_{tAD}$, $V_{tBC}$, and $V_{tEF}$ are velocity of the leaflet tips at inlet, outlet and the arbitrary section, "a" is the major diameter of the elliptic housing, $\theta$ is the angular motion of the leaflet and Vi is the velocity of the control volume. By solving Eqs. (1) to (4) the reaction force applying on the leaflet ($F_{reac}$) is calculated. $F_{reac}$ is also calculated differently as follows, starting by considering the same control volume. There are two forces applying on the inlet (AD) (AD $P_{ao}$ and $\dot{m}_{AD}V_{AD}$), and two forces on the outlet (BC) (BC $P_v$ and $\dot{m}_{BC}V_{BC}$) as shown in FIG. 7.

Figure 8:
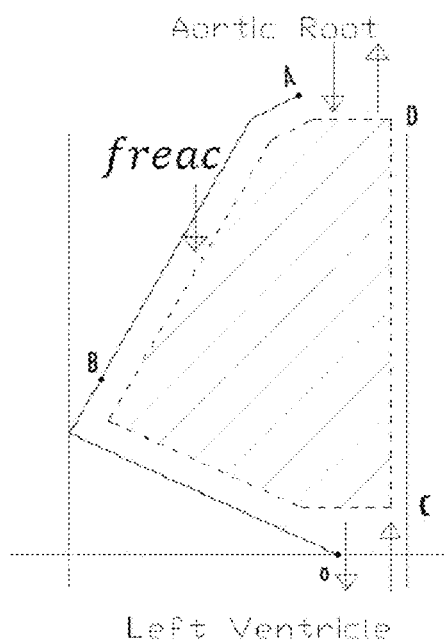
FIG. 8 depicts a half model of a valve in an arbitrary position. In the diagram, the control volume is considered from outside. Arrows show the moment and forces applying on the leaflets in an arbitrary position (top). Flow chart of the numerical model proposed in the study (bottom).
Figure 8:
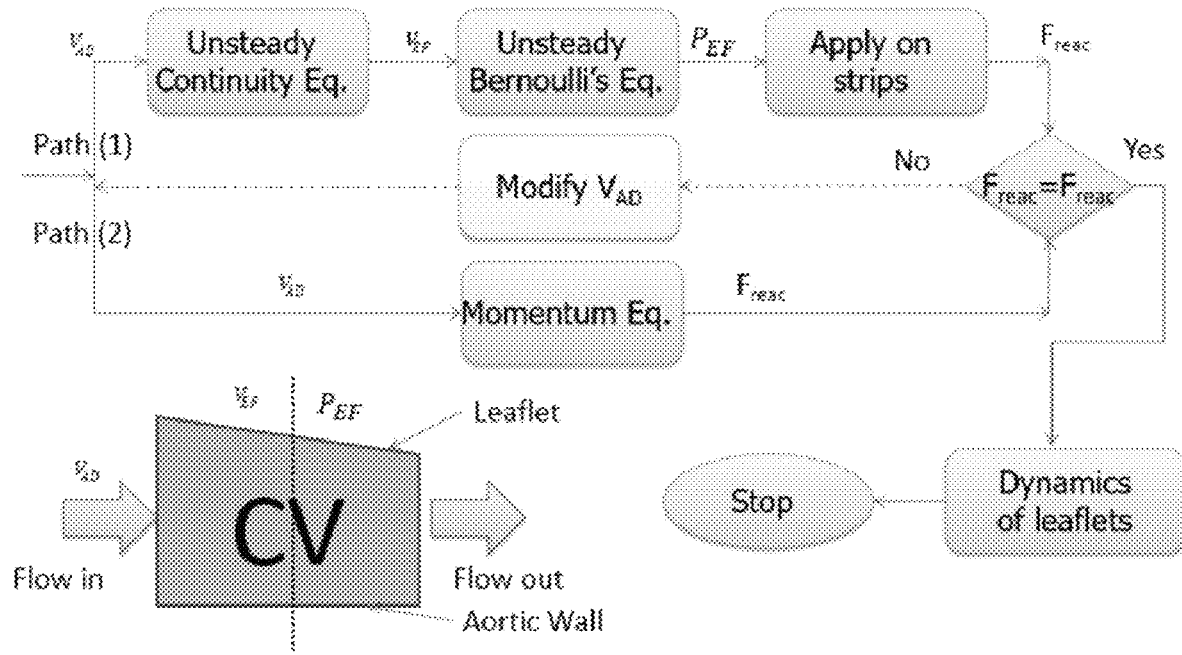

As shown in FIG. 8, all these forces must be in equilibrium with $F_{reac}$ and the momentum change in the control volume, dMV/dt, as such:

$$(a\ AD\ P_{ao} - a\ BC\ P_v - F_{reac}) - (\dot{m}_{BC}V_{BC} - \dot{m}_{AD}V_{AD}) = \frac{dMV}{dt} \quad (5)$$

$$\dot{m}_{BC} = \rho\ a\ BC(V_{BC} - V_{tBC}) \quad (6)$$

$$\dot{m}_{AD} = \rho\ a\ AD(V_{AD} - V_{tAD}) \quad (7)$$

Here, the mass of the control volume (M) and its velocity (V) are calculated as such:

$$M = \rho\ a\ CD\frac{AD+BC}{2}\sin\theta \quad (8)$$

$$V = \frac{V_{AD}+V_{BC}}{2} \quad (9)$$

$\rho$ is the blood density and $V_{tBC}=-OB\ \omega\ \cos\theta$ and $V_{tAD}=-OA\ \omega\ \cos\theta$. Eqs. (5) to (9) are solved for $F_{reac}$, which was calculated earlier using Eqs. (1) to (4). The following energy equations for a control volume with moving boundaries are used to calculate the final values of velocities and pressures, as such (Mohammadi H, et al, 2017, Cardiovascular Systems, 5(2)):

$$\frac{V_{AD}^2 - V_{EF}^2}{2} = \int^Y \frac{dV}{dt}dy - \frac{P_{AD}-P_{EF}}{\rho} \quad (10)$$

$$\frac{dV}{dt} = [(V_j)_t - (V_j)_{t-\delta t}]/\delta t \quad (11)$$

$$\int_0^Y \frac{dV}{dt}dy = \sum_{j=1}^N \frac{[(V_j)_t - (V_j)_{t-\delta t}]}{\delta t}\delta(zh)\sin\theta \quad (12)$$

$$\delta(zh) = \frac{r}{N} \quad (13)$$

Using the equation expressing the dynamic motion of the leaflet: MP+Mg=Jpω the angular position of the leaflet with respect to time is calculated. Here MP is the pressure induced moment, Mg is the gravity induced moment, and Jp is the angular mass of leaflets with respect to hinges:

$$M_P = -\int_N^r (P_{EF} - P_{AD}) a\, OE\, dl = \sum_{n=1}^{N} (P_{EF} - P_{AD}) a\, OE\, \delta l \quad (14)$$

$$T_g = mg\, (b/2)\cos\theta \quad (15)$$

Here, m denotes the mass of a single leaflet. The 205 leaflet's motion begins based on the maximum opening angle of the leaflets which is set to 89° (initial velocity=0 m/s). The assessment of the regurgitation flow is based on $Q_{rf}=A_{or}V_i\delta t$, here, $A_{or}$ refers to the total orifice area.

Modeling Setups:

The objective here is to estimate the regurgitation flow volume in a complete cardiac cycle. The time increment δt was set to 0.05 ms. Because $F_{reac}$ is calculated based on two different methods, convergence was assumed to take place when the deterrence between the numerical valves for it becomes less than or equal to 0.01 (N). The number of strips (N) was chosen as 45 and the Runge-Kutta method of the $4^{th}$ order was implemented to solve the differential equations. The heart rate (HR) was set as 70 beats per minute (bpm) and the cardiac output (CO) to 6l/min. The average aortic pressure was chosen to be 16.0 kPa or 120 mmHg.

Experimental Procedure:

The in vitro testing was performed using the ViVitro Systems Inc. pulse duplicator with an additional customized modulus known as Leonardo VSI (FIG. 9). This system mimics the performance of the left ventricle by generating pulsatile flow through prosthetic heart valves placed in the aortic or mitral position. In this platform, pulse rate, cardiac output and pressures are set to 70 beats/min, 5 L/min and nearly 120/80 mmHg, respectively. The Leonardo VSI is equipped with a high spaciotemporal resolution capability of nearly 0.001 cm² and 22 μs (Scotten L S, Siegel R, 2014, Ann Transl Med., 2(5):43). This apparatus measures the projected dynamic valve area (PDVA) from the bottom (upstream) of the valve. A Viscoelastic Impedance Adapter VSI (VIA) is also provided between the pump and the left ventricle for the adjustment of viscoelastic and isovolumetric functionality. This physiological 225 attribute matches with periods of valve opening and closure. The operational fluid implemented was saline with viscosity 1 mPa·s and density of 1.0 g/ml (Scotten L S, Siegel R, 2011, The Journal of Heart Valve Disease, 20:664-672). The apex valve mounted in the Leonardo apparatus is shown in FIG. 9.

Results and Discussion

Figure 10:
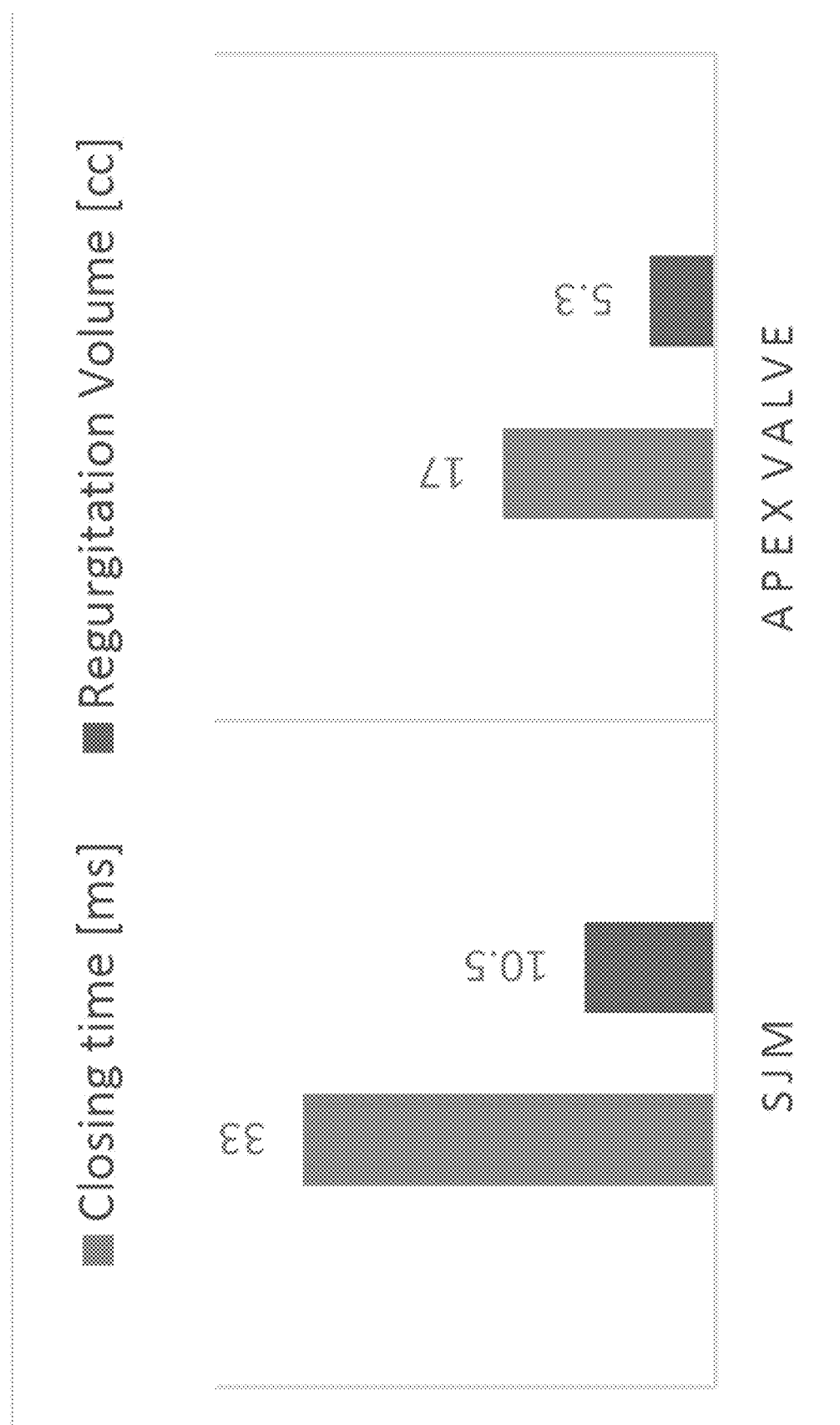
FIG. 10 depicts the regurgitation flow volume and closing time for an SJM valve and apex valve.

In this study, the velocities of blood flow (regurgitation flow velocity) and leaflet tip and the regurgitation volume for the apex and St. Jude Medical valves were calculated. In order to calculate the regurgitation volume, the relative velocity between the leaflet tips and the blood in the vicinity was taken into consideration. The closing time for the apex valve falls within the ranges of 15 to 18 ms whereas the conventional SJM model offers a longer closing time ranging from 26 to 33 ms that highly depends on the size of the valve. The velocity of blood flow which represents the closing volume ranges from 1.6 m/s to 2.1 m/s in the apex valve whereas the same velocity in the SJM model is calculated to be 2.7 m/s to 2.9 m/s. A lower regurgitation velocity leads to a softer closure of the valve which is a highly desirable in the design of mechanical heart valves. The closing volume or regurgitation flow volume and the closing time of the leaflet were shown in FIG. 10. The closing time for the SJM bileaflet valve was reported to be 33 ms which is consistent with previous studies (Mohammadi H, et al, 2017, Cardiovascular Systems, 5(2)). The closing time for the apex valve was calculated to be 17 ms. This closing time and the blood velocity result in the regurgitation flow volume to be 10.5 cc for SJM model and valve 5.3 for the apex valve. It was previously computationally shown that applying 10% ovality on the housing significantly improves the hemodynamics and efficiency of St. Jude Medical valve (Mohammadi H, et al, 2017, Cardiovascular Systems, 5(2)).

Figure 11:
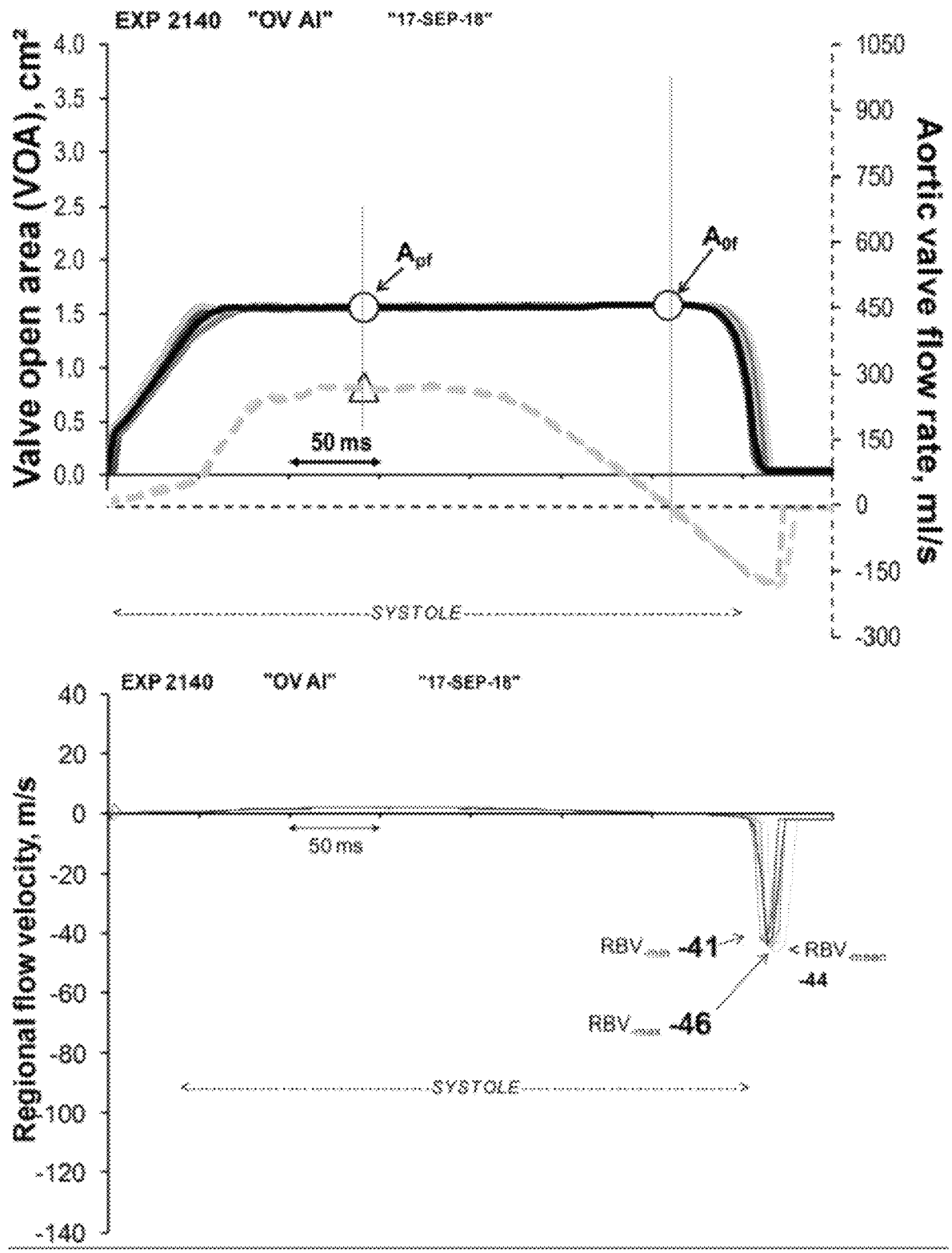
FIG. 11 depicts the hemodynamic performance of the apex valve in systole on the ViVitro Pulse Duplicator apparatus, which is characterized by the valve open area (VOA), aortic valve flow rate and the regurgitation backflow velocity (RBV). A0f=VOA at zero flow rate crossover where valve closing regurgitation begins (start of negative flow rate), Apf=the valve is fully open. Experimental analysis was performed 5 times (N=5) and all the experimental results have been superimposed and presented together.

The numerical results are also fully consistent with the experimental results as shown in FIG. 11. The valve open area (cm²), aortic valve backflow rate (ml/s) and regional flow velocity are all plotted with respect to time (s). As shown in FIG. 11, The closing volume is the area of the curve where aortic valve flow rate has a negative value. The closing volume is estimated to be approximately 5 cc/cycle (also estimated by the proposed model), which is in the range similar to that of bioprosthetic valve (Scotten L S, Siegel R, 2014, Ann Transl Med., 2(5): 43). Also, results show that the time when the valve is fully open until it is fully closed, i.e. the closing time, is approximately 35 ms (also estimated by the proposed model). Interestingly, the regional backflow velocity (RBV) maintains an average value of 44 m/s for the apex valve. Similar value for the SIM valve with the same size is larger than 100 m/s and for bioprosthetic valves is 10 to 30 m/s. Offering such RBV by the OV which is closer to that of bioprosthetic valve is of particular importance. This is because smaller RBV in a prosthetic valve leads to less thrombogenic complications.

In general, the higher these transients are, the more the valve thrombogenic potential. Mechanical valves prostheses are known to have an enormous backflow velocity spike near the instant of closure which is much less compared with tissue valves which is thought to be the main reason for mechanical valves thrombogenicity in contrast to tissue valves. This issue in the apex valve is properly addressed.

CONCLUSION

The major issue with all previous bileaflet mechanical heart valve models is that there are three orifices (two major and one minor) incorporated into their design, which essentially divide the blood flow into three main streams and that the leaflets play the role of serious obstacle for the blood flow. There is no question that this is a major issue with their design which needs to be properly addressed. The OV is the only bileaflet mechanical heart valve that provides only one major orifice for the blood flow which is very comparable to the design of tissue valves. Previously, it was computationally shown that applying 10% ovality on the housing significantly improves the hemodynamics and efficiency of St. Jude Medical valve. This design feature was incorporated into the proposed valve. If the valve is viewed from top, it is 10% oval (or nearly elliptic). There are 3 key design features incorporated into the design of the housing. (1) The saddle shaped housing is essential in order to accommodate the range of motion considered for the leaflets, (2) the housing prevents a full contact (planar) between the leaflets and the housing in order to prevent RBC lysis, and (3) the housing is low profile in order to minimize the transvalvular pressure required.

In all conventional models such as SJM, Medtronic, and On-X, the leaflets are flat and remain directly in the path of the highest blood flow velocity when open. The leaflets of the apex valve, however, have a unique design and not just a simple curve. When the valve is fully open, the leaflets form a cylindrical shell with the housing featuring an oval cross section. This design feature gives two significant assets to the valve: (1) the effective orifice area in the proposed valve is maximized which is directly comparable to that of bioprosthetic valves unlike all of the existing mechanical valves, and (2) blood flows through one main orifice, rather than being separated and essentially disturbed by flowing through three orifices at different velocities as in conventional models.

Figure 12:
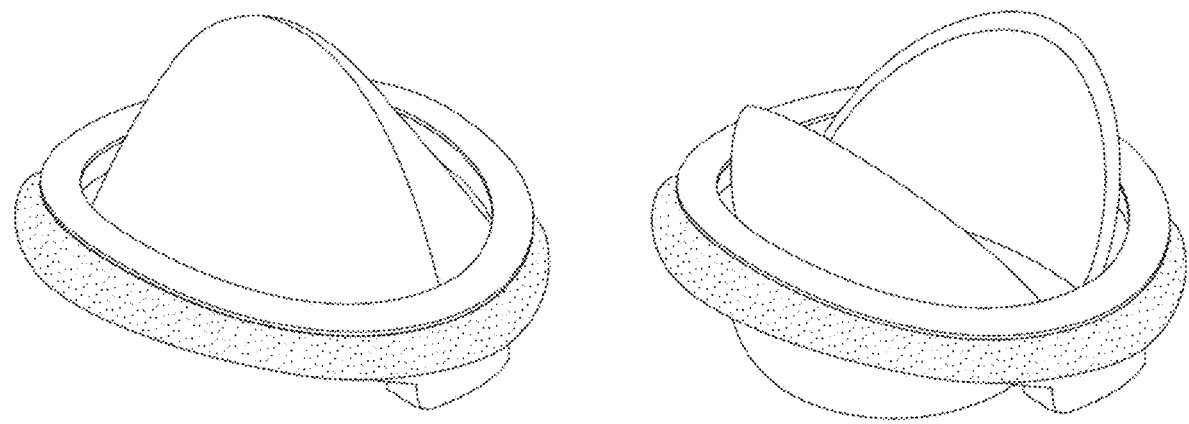
FIG. 12 depicts (a) isometric views of the valve in the fully closed and fully open phases. The whole assembly, the location of hinges, the sewing ring are all clearly shown, (b) the prototype of the apex valve 3D printed using aluminum. It should be noted that in this phase hinges are shown as pin connected for demonstration purposes.
Figure 12:
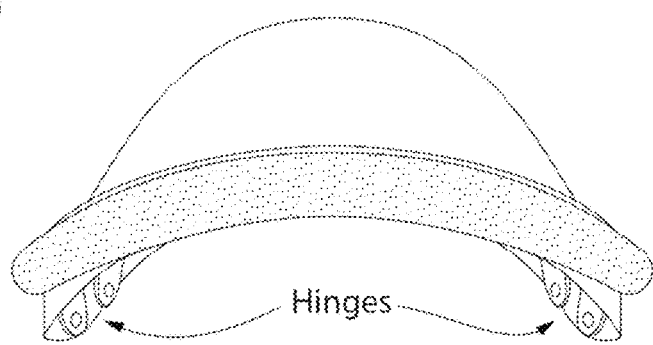
Figure 12:
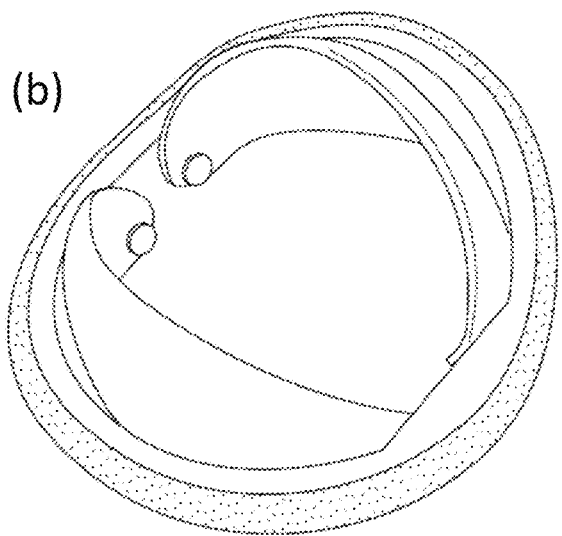

The design of the hinge follows that of SJM model with one significant change. The butterfly socket is provided on the leaflets and not on the housing. This is extremely important because the hinges are exposed to more blood flow in comparison with all other conventional valves such as SJM, Medtronic, and On-X. This means the hinge area would receive a more effective wash (shear stress). The assembled valve in both the closing and opening phases is shown in FIG. 12. "In the offered numerical model in this study, the valve model was considered to be half symmetrical that needs to be addressed in future studies. In reality the aortic root is not symmetrical. In fact, the geometry of the aortic root including the valve and the sinuses and the hemodynamics around the valve are highly related.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A mechanical bileaflet heart valve device, comprising:
   a ring-like housing having a saddle-shaped curvature and an elliptical top-down profile that defines an elliptical central orifice for blood flow therethrough; and
   two substantially hollow cylindrical-wedge-shaped curved leaflets hingedly attached to an interior of the housing, wherein each leaflet is rotatable between a closed position that completely seals the central orifice and an open position that completely opens the central orifice; and
   wherein the central orifice comprises a major axis diameter and a minor axis diameter, and the major axis diameter is between about 15 mm and 40 mm.

2. The device of claim 1, wherein the minor axis diameter is between about 10 mm and 35 mm.

3. The device of claim 1, wherein the saddle-shape curves downwards towards the major axis diameter and curves upwards towards the minor axis diameter.

4. The device of claim 1, wherein the leaflets are hingedly attached to the housing at opposing downward curving sections adjacent to the major axis diameter.

5. The device of claim 1, wherein the housing comprises an opposing pair of inward facing semi-spherical nodal bumps positioned on opposing upward curving sections in alignment with the minor axis diameter.

6. The device of claim 5, wherein each leaflet rests against each nodal bump in the open position.

7. The device of claim 1, wherein the cylindrical-wedge-shape of the leaflets comprises two curved lateral halves that curve symmetrically from a central crest and terminate in two opposing tips, each tip comprising an outward facing hinge projection.

8. The device of claim 7, wherein the hinge projections of the leaflets engage inward facing hinge sockets in the housing to form the hinged attachment between the leaflets and the housing.

9. The device of claim 8, wherein the hinged attachment is configured to be exposed to and continually washed by a flow of blood such that thrombosis incidence is reduced.

10. The device of claim 8, wherein the hinge projections and the hinge sockets each comprise a substantially hourglass shape.

11. The device of claim 10, wherein the hinge projection is slightly smaller than the hinge socket, such that a degree of sliding motion is achievable between the leaflets and the housing.

12. The device of claim 1, wherein the leaflets each comprise a superior curved leading edge and an inferior curved trailing edge.

13. The device of claim 12, wherein the leading edges of the leaflets meet each other in a center of the central orifice and the trailing edges of the leaflets meet the housing in the closed position.

14. The device of claim 12, wherein the leading edge is configured to travel for a travel angle between the closed and open positions, wherein the travel angle is between about 30° and 50°.

15. The device of claim 12, wherein the trailing edge is formed at an angle above a horizontal plane, wherein the angle is between about 0° and 25°.

16. The device of claim 15, wherein the trailing edge is formed at an angle above a horizontal plane, wherein the angle is half of the travel angle.

17. The device of claim 1, wherein the housing comprises a sewing ring positioned on an outward facing surface.

18. The heart valve prosthesis of claim 1, wherein the sewing ring is made of a woven or knitted fabric.

19. A mechanical bileaflet heart valve device, comprising:
    a ring-like housing having a saddle-shaped curvature and an elliptical top-down profile that defines an elliptical central orifice for blood flow therethrough; and
    two substantially hollow cylindrical-wedge-shaped curved leaflets hingedly attached to an interior of the housing, wherein each leaflet is rotatable between a closed position that completely seals the central orifice and an open position that completely opens the central orifice;
    wherein the central orifice comprises a major axis diameter and a minor axis diameter, and the minor axis diameter is between about 10 mm and 35 mm.

20. A mechanical bileaflet heart valve device, comprising:
    a ring-like housing having a saddle-shaped curvature and an elliptical top-down profile that defines an elliptical central orifice for blood flow therethrough; and
    two substantially hollow cylindrical-wedge-shaped curved leaflets hingedly attached to an interior of the housing, wherein each leaflet is rotatable between a closed position that completely seals the central orifice and an open position that completely opens the central orifice;
    wherein the central orifice comprises a major axis diameter and a minor axis diameter, and the housing comprises an opposing pair of inward facing semi-spherical nodal bumps positioned on opposing upward curving sections in alignment with the minor axis diameter.

21. A mechanical bileaflet heart valve device, comprising:
a ring-like housing having a saddle-shaped curvature and an elliptical top-down profile that defines an elliptical central orifice for blood flow therethrough; and
two substantially hollow cylindrical-wedge-shaped curved leaflets hingedly attached to an interior of the housing, wherein each leaflet is rotatable between a closed position that completely seals the central orifice and an open position that completely opens the central orifice;
wherein the cylindrical-wedge-shape of the leaflets comprises two curved lateral halves that curve symmetrically from a central crest and terminate in two opposing tips, each tip comprising an outward facing hinge projection; and
wherein the hinge projections of the leaflets engage inward facing hinge sockets in the housing to form the hinged attachment between the leaflets and the housing.

22. A mechanical bileaflet heart valve device, comprising:
a ring-like housing having a saddle-shaped curvature and an elliptical top-down profile that defines an elliptical central orifice for blood flow therethrough; and
two substantially hollow cylindrical-wedge-shaped curved leaflets hingedly attached to an interior of the housing, wherein each leaflet is rotatable between a closed position that completely seals the central orifice and an open position that completely opens the central orifice;
wherein the leaflets each comprise a superior curved leading edge and an inferior curved trailing edge; and
wherein the leading edge is configured to travel for a travel angle between the closed and open positions and the travel angle is between about 30° and 50°.

23. A mechanical bileaflet heart valve device, comprising:
a ring-like housing having a saddle-shaped curvature and an elliptical top-down profile that defines an elliptical central orifice for blood flow therethrough; and
two substantially hollow cylindrical-wedge-shaped curved leaflets hingedly attached to an interior of the housing, wherein each leaflet is rotatable between a closed position that completely seals the central orifice and an open position that completely opens the central orifice;
wherein the leaflets each comprise a superior curved leading edge and an inferior curved trailing edge; and
wherein the trailing edge is formed at an angle above a horizontal plane, wherein the angle is between about 0° and 25°.

* * * * *